US011164134B2

(12) United States Patent
Barak et al.

(10) Patent No.: US 11,164,134 B2
(45) Date of Patent: Nov. 2, 2021

(54) SYSTEMS AND METHODS FOR IMPROVING PROCESS SAFETY IN AN INDUSTRIAL ENVIRONMENT

(71) Applicant: NEW GO—ARC (2015) LTD., Motza Illit (IL)

(72) Inventors: Dror Barak, Motza Illit (IL); Haim Ygal Srur, Tel Aviv (IL); Hana Gur Arie, Modi'in-Maccabim-Re'ut (IL); Roy Daya, Kfar Haoranim (IL)

(73) Assignee: NEW GO—ARC (2015) LTD., Motza Illit (IL)

( * ) Notice: Subject to any disclaimer, the term of this patent is extended or adjusted under 35 U.S.C. 154(b) by 0 days.

(21) Appl. No.: 16/799,203

(22) Filed: Feb. 24, 2020

(65) Prior Publication Data

US 2020/0193341 A1    Jun. 18, 2020

Related U.S. Application Data

(63) Continuation of application No. PCT/IL2018/051066, filed on Sep. 23, 2018.
(Continued)

(51) Int. Cl.
*G06Q 10/06* (2012.01)
*G06Q 50/26* (2012.01)

(52) U.S. Cl.
CPC ... *G06Q 10/0635* (2013.01); *G06Q 10/06375* (2013.01); *G06Q 10/063112* (2013.01); *G06Q 10/063114* (2013.01); *G06Q 50/265* (2013.01)

(58) Field of Classification Search
None
See application file for complete search history.

(56) References Cited

U.S. PATENT DOCUMENTS 7,233,781 B2    6/2007  Hunter
9,905,107 B2 *  2/2018  Chong ............... G08B 21/0423
(Continued)

FOREIGN PATENT DOCUMENTS

WO    2008105578 A1    9/2008

OTHER PUBLICATIONS

Jung, Jieun, and Byunghun Song. "The possibility of wireless sensor networks for industrial pipe rack safety monitoring." 2014 47th Hawaii International Conference on System Sciences. IEEE, 2014. (Year: 2014).*
(Continued)

*Primary Examiner* — Thomas L Mansfield
(74) *Attorney, Agent, or Firm* — Browdy and Neimark, PLLC

(57) ABSTRACT

Systems and methods use for improving process safety. In one implementation, a system may determine least one characteristic of a task scheduled to take place in an industrial environment. The system may use first synergy data from at least three types of safety-related information and the at least one characteristic of the task to determine that a predicted risk score of the scheduled task is below a first threshold. Thereafter, the system may obtain real-time information indicative of the integrity of an industrial apparatus. The system may use second synergy data indicative of a change in the integrity of industrial apparatus and real-time information to determine that an actual risk score of the task has changed from the predicted risk score. When the actual risk score of the task is above a second threshold, the system may initiate a remedial action to manage a hazard associated with process safety.

19 Claims, 10 Drawing Sheets

Related U.S. Application Data

(60) Provisional application No. 62/562,501, filed on Sep. 25, 2017.

(56) References Cited

U.S. PATENT DOCUMENTS

| | | | | |
|---|---|---|---|---|
| 2003/0050725 | A1* | 3/2003 | Dirnfeldner | G05B 19/408 700/174 |
| 2008/0177994 | A1* | 7/2008 | Mayer | G06F 9/4418 713/2 |
| 2009/0089108 | A1 | 4/2009 | Lee et al. | |
| 2011/0037571 | A1 | 2/2011 | Johnson, Jr. et al. | |
| 2012/0146789 | A1* | 6/2012 | De Luca | H04N 3/38 340/540 |
| 2012/0198464 | A1* | 8/2012 | Taira | G06F 9/5077 718/103 |
| 2012/0299727 | A1* | 11/2012 | Newman | G05B 23/0267 340/540 |
| 2015/0346706 | A1* | 12/2015 | Gendelman | G05B 19/058 700/79 |
| 2016/0307425 | A1* | 10/2016 | Jobin | G08B 21/182 |
| 2017/0343966 | A1* | 11/2017 | Schadow | G05B 11/06 |
| 2018/0001184 | A1* | 1/2018 | Tran | G06F 1/163 |

OTHER PUBLICATIONS

Musu, C., V. Popescu, and D. Giusto. "Workplace safety monitoring using RFID sensors." 2014 22nd Telecommunications Forum Telfor (TELFOR). IEEE, 2014. (Year: 2014).*

* cited by examiner

SYSTEMS AND METHODS FOR IMPROVING PROCESS SAFETY IN AN INDUSTRIAL ENVIRONMENT

CROSS REFERENCES TO RELATED APPLICATIONS

This application claims the benefit of priority of U.S. Provisional Patent Application No. 62/562,501, filed on Sep. 25, 2017, which is incorporated herein by reference in its entirety.

BACKGROUND

I. Technical Field

The present disclosure generally relates to preventing work accidents, and more specifically to systems, methods, and devices that use a dynamic risk analysis to evaluate a risk of a task.

II. Background Information

Workplace safety remains a crucial issue in many regions of the globe. The two main challenges most workplaces deal with on a daily basis are the personal safety issues and process safety issues. Most personal safety issues are caused by the performance gap and the knowing-doing gap. The performance gap that exists between the accepted practice and actual execution is caused by unskilled workers with high turnover rates and lack of alertness to possible hazards. The knowing-doing gap exists in two levels. The first, between the knowledge a worker has on work procedures and the way the worker actually acts. The second between the amount of data an organization has and the actual events it prevents. Typicality, the knowing-doing gap in safety is caused by the inability to see the whole picture in real-time and the failure separates the wheat from the chaff. The existence of the performance gap and the knowing-doing gap in workplaces is evident because despite training, same accidents are repeated.

Typically, process safety issues are caused when industrial apparatuses (e.g., machines, structures, silos, and more) are built, used, or maintained without complying with regulations. The goal of personal safety is protecting employees from injury and illness. In contrast, the goal of process safety is protecting capital assets and environment from catastrophic accidents and near misses, particularly structural collapse, explosions, fires, and toxic releases. These two challenges may be managed hand in hand because promoting personal safety can result in improvement in equipment and operational integrity, and promoting process safety can result in lowering the risk of injury and human life loss.

With the rise of the Internet of Things (IoT), many workplaces, are able to obtain a large amount of data monitoring different aspects in the workplace. Nevertheless, collecting all this data will not end personal accidents and process accidents, because current safety systems do not sufficiency account for the human factor. Moreover, current safety systems always provide static instructions to employees while their tasks are dynamic in nature and the risk keep changes. Consequently, current safety systems fail to identify and address hazards before preventable accidents occur.

The disclosed systems and methods are directed to providing a new solution for creating a safe work environment that fundamentally takes into consideration the human factor. The suggested systems and methods continuously identify hazards by choosing relevant data originating from different sources, calculate the current risk score, and initiate actions to prevent personal accidents and process accidents.

SUMMARY

Embodiments consistent with the present disclosure provide systems and methods for initiating a remedial action to prevent an accident in an industrial environment.

In one embodiment, a method for preventing work accidents is provided. The method may include receiving details of a task scheduled to take place in an industrial environment; retrieving from a memory device data associated with the industrial environment, wherein the retrieved data includes historical safety-related information; and using the retrieved data and the received details to determine at least one characteristic of the task. Before the task take place, the method may include obtaining at least three types of safety-related information associated with the task scheduled to take place in the industrial environment; determining first synergy data from the at least three types of safety-related information and the at least one characteristic of the task; and determining from the first synergy data when a predicted risk score of the scheduled task is below a first threshold. While the task is taking place, the method may include obtaining real-time information indicative of human error of at least one employee associated with the task; determining second synergy data from the at least three types of safety-related information and the real-time information; and determining from the second synergy data when an actual risk score of the task has changed from the predicted risk score. When the actual risk score of the task is above a second threshold, the method may include initiating a remedial action to prevent an accident.

In another disclosed embodiment, a system for preventing work accidents is provided. The system may include a network interface configured to receive details of a task scheduled to take place in an industrial environment, a memory configured to store data associated with the industrial environment, and at least one processor. The at least one processor ay be configured to retrieve from the memory data associated with the industrial environment, wherein the retrieved data includes historical safety-related information; and use the retrieved data and the received details to determine at least one characteristic of the task. Before the task take place, the at least one processor may obtain at least three types of safety-related information associated with the task scheduled to take place in the industrial environment; determine first synergy data from the at least three types of safety-related information; and determine from the at least one characteristic and the first synergy data when a predicted risk score of the scheduled task is below a first threshold. While the task is taking place, the at least one processor may obtain real-time information indicative of human error of at least one employee associated with the task; determine second synergy data from the at least three types of safety-related information and the real-time information; and determine from the second synergy data a change in the risk score of the task. When an actual risk score of the task is above a second predetermined threshold, the at least one processor may initiate a remedial action to prevent an accident.

Consistent with other disclosed embodiments, non-transitory computer-readable storage media may store program instructions, which are executed by at least one processing device and perform any of the methods described herein.

The foregoing general description and the following detailed description are exemplary and explanatory only and are not restrictive of the claims.

BRIEF DESCRIPTION OF THE DRAWINGS

The accompanying drawings, which are incorporated in and constitute a part of this disclosure, illustrate various disclosed embodiments. In the drawings.

DETAILED DESCRIPTION

Figure 1:
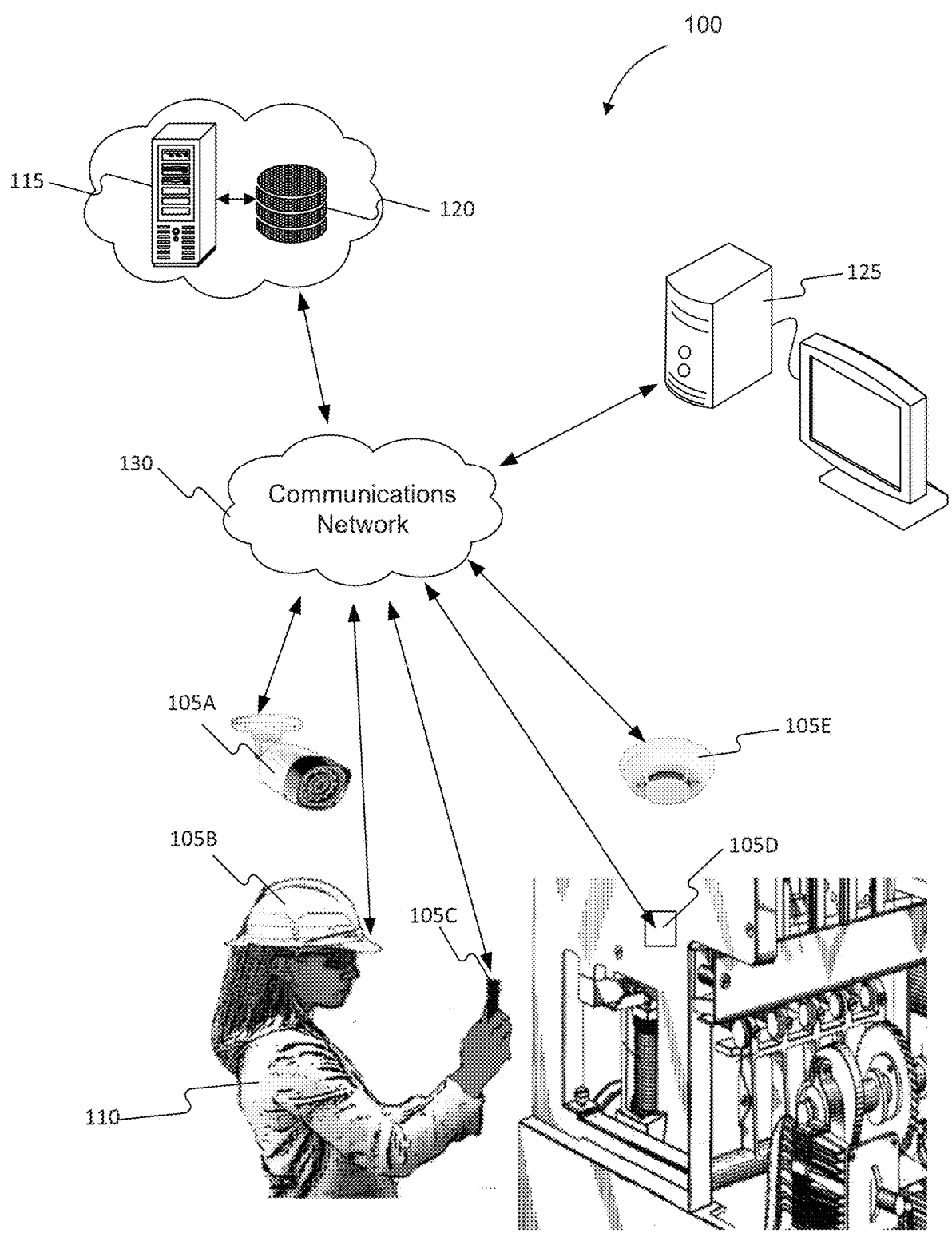
FIG. 1 is an illustration of an exemplary system for analyzing information collected from an industrial environment.

The following detailed description refers to the accompanying drawings. Wherever possible, the same reference numbers are used in the drawings and the following description to refer to the same or similar parts. While several illustrative embodiments are described herein, modifications, adaptations and other implementations are possible. For example, substitutions, additions or modifications may be made to the components illustrated in the drawings, and the illustrative methods described herein may be modified by substituting, reordering, removing, or adding steps to the disclosed methods. Accordingly, the following detailed description is not limited to the disclosed embodiments and examples. Instead, the proper scope is defined by the appended claims.

Term Definitions

The present disclosure is directed to preventing accidents (e.g., work accidents) in an industrial environment. As used herein, the term "industrial environment" refers to workplaces, establishments, or areas in which workers manufacture, produce, store, assemble, refine, construct, or otherwise change the composition, phase, physical and/or chemical characteristics of a material or fluid. Examples of industrial environments include factories, manufacturing plants, refineries, fabrication facilities, warehouses, construction areas, drilling rigs, offshore platforms, and more. Typically, each industrial environment may be associated with its own work procedures. The term "work procedures" refers to instructions for completing a task. For example, the work procedures may include written instructions that describe the safest and most efficient way for completing a task. In one case, the work procedures may include a step by step description of a process associated with a task and any deviation from that process may cause damage or loss.

Embodiments of the present disclosure include receiving details of a task scheduled to take place in the industrial environment. As used herein, the term "task" in the context of this disclosure refers to one or more actions done by at least one employee, who perform his/her work duties. The one or more actions may include: transporting material from one place to another, bringing a piece from an initial state to a final state, fixing a specific malfunction in a machine, and more. The task may be a routine task that is part one employee's daily work, or a special task that is assigned to at least one employee in response to a situation in the industrial environment. The terms "worker" and "laborer" may also be used interchangeably in this disclosure with reference to an employee. The term "details of a task scheduled to take place" refers to any type of data that describes a task or data associated with the task. For example, the details of the task may include a description of the desired outcome of the task, a description of the cause of the task, a list of employees assigned to the task, and more. In one embodiment, the details of the task may be obtained by receiving a request form, such as a work order. In another embodiment, the details of the task may be obtained by receiving a malfunction report.

Embodiments of the present disclosure further include determining at least one characteristic of the task. As used herein, the term "characteristic of the task" refers to one or more features attributed to the task. Consistent with the present disclosure, the characteristic of the task may assist in making a task measurable and controllable. For example, the characteristic of the task may be associated with the amount of resources (financial, equipment, manpower, materials and tools) required to complete the task, the amount of man-hours required to complete the task, the expected length of the task, or the purpose and value of the task. In one embodiment, the characteristic of the task may include at least one of the following: estimated start time of the task, identity of employees expected to participate in the task, expected duration of the task, potential accidents associated with the task, potential accidents associated with the identity of employees, types of materials expected to be used in the task, and types of tools expected to be used in the task. The term "tool" refers to a manually operated device for performing a task. In the context of this disclosure, a tool can vary from a screwdriver and a jackhammer to a forklift truck and an excavator.

Embodiments of the present disclosure further include obtaining safety-related information associated with the task scheduled to take place in the industrial environment. As used herein, the term "safety-related information" refers to any type of information associated with the safety aspects of a task. Consistent with the present disclosure, the safety-related information may include work procedures associated with the task (e.g., the required safety measures for the task, the minimum number of people required to complete the task, etc.), information associated with an employee assigned to the scheduled task (e.g., information about an employee's current shift and previous shifts, information about the employee's qualifications and seniority, etc.), information associated with a location of the scheduled task (e.g., details of other tasks scheduled to take place at a same area, safety restrictions applied to the location, etc.), information associated with the scheduled task (e.g., the individual responsible for the task, the budget for the task, etc.), information associated with tools expected to be used in the scheduled task (e.g., a list of tools that can be used in this task, indication of permits required to operate certain tools, etc.), information associated with materials expected to be used in the scheduled task (e.g., a list of materials expected to be used in the task, restrictions associated with materials expected to be used in the task, etc.), information associated with a time of the scheduled task (e.g., deadline for completing the task, expected duration etc.), information about calendar events (e.g., information about holidays or special events, information about personal events of employees assigned to the task, etc.), information associated with the expected weather for the duration of the scheduled task (e.g., predicted rain falls, wind speed, etc.), information from periodic inspection tours (e.g., known locations of safety hazards, warnings on certain working tools, etc.), information associated with the industrial environment (e.g., infrastructure blueprints, machinery inventory, material inventory, general regulations and specific procedures, a risk analysis plan, etc.), and more.

Embodiments of the present disclosure, further include obtaining real-time information indicative of human error of at least one employee associated with the task. As used herein, the term "real-time information", in the context of this disclosure, refers to information associated with events happened in the industrial environment that is obtained by the system substantially while the events happen. In one embodiment, the system may receive the real-time information in less than about one minute from the time the information was captured. In other embodiments, the system may receive the real-time information in less than about 30 seconds, in less than about 15 seconds, in less than about five seconds, in less than about one second from the time the information was captured. An example type of real-time information that may be obtained is image data, e.g., from a closed-circuit television system. Other types of real-time information may be obtained from a multiple cameras located in the industrial environment, one or more communication device of employees in the industrial environment, wearable sensors on employees in the industrial environment, operational technology (OT) sensors, environmental sensors, sensors associated with working tools, and more. Consistent with the present disclosure, the real-time information may be indicative of human error of at least one employee associated with the task. In order to know that at least one employee made an error, the system may compare the obtained real-time information with the work procedures and/or with a predetermined behavior baseline for each employee associated with the task to determine if a deviation exists. For example, the system may know that after a certain material is added to a chemical reactor, the mixture should be heated to 60°. In this example, the system may initiate a remedial action when it obtains information indicating that the mixture is about to be heated to 90°. Examples of real-time information may include detected changes in the performances of an employee assigned to the task, detected changes in planned locations of the task, detected changes in tools expected to be used in the task, detected changes in materials expected to be used in the task, detected changes in an expected start time of the task, detected changes in an expected weather during the task, detected changes in the operational integrity of apparatuses in the industrial environment, detected changes in the structural statuses of facilities in the industrial environment, and more.

The present disclosure further includes determining first synergy data safety-related information and task characteristics, and determining second synergy data from the safety-related information and the real-time information. As used herein, the term "determining synergy data" refers to a process of cross-reference information from multiple sources and identifying events that may be unidentifiable when considering information from each source separately. In one embodiment, the first synergy data may include details of at least one handover event expected to happen while the task is taking place. The handover event may be an employee shift change during the task, a material change during the task, a tool change during the task, a supervisor change during the task, and a change from working during day time and nighttime. In another embodiment, the second synergy data may include details on a situation in the industrial environment that deviates from work procedures of the industrial environment. For example, the industrial environment may have a number of work procedures for storing different materials. The second synergy data may include an indication that a worker had stored a material not where the material should have been stored.

Embodiments of the present disclosure further include determining a predicted risk score of the scheduled task and determining a change in the risk score of the task. As used herein, the term "risk score" refers to a score that can be assigned based on comparing synergy data to a risk predictor model. A risk score can have a standard value (e.g., a number) or a multi-value threshold (e.g., a line on a graph). The value of the risk score may correlate to the deviation, upwards or downwards, from a reference risk score associated with a specific task or a reference risk score associated with a general task. In certain embodiments, if a risk score is greater than a reference risk score, there is increased likelihood that an undesirable event that may involve physical damages to workers or machines will occur during or after the task. In some embodiments, the magnitude of a predicted risk score or the amount by which it exceeds a reference risk score, may be indicative of the risk associated with a scheduled task. Consistent with the present disclosure, the system may receive real-time information and update the risk score based on events detected using the real-time information. When the actual risk score of a task is above a certain threshold, the system may initiate a remedial action to prevent a work accident. As used herein, the term "initiating a remedial action" generally refers to any action that the system triggers to prevent hazardous events in the industrial environment or to minimize the damage of such events. Examples of remedial actions, include transmitting location-based warning messages to employees, displaying the detected hazards on a personalized map, performing an automatic shutdown, and creating customized inspection tour based on the detected locations of the plurality of hazards.

Reference is now made to FIG. 1, which shows an example of a system 100 for analyzing information collected from an industrial environment. In one embodiment, system 100 may represent a computer-based system that includes computer system components, desktop computers, workstations, tablets, handheld computing devices, memory devices, and/or internal network(s) connecting the components. System 100 may include or be connected to various network computing resources (e.g., servers, routers, switches, network connections, storage devices, etc.) necessary to support the services provided by system 100. In one embodiment, system 100 enables obtaining safety-related information associated with a task scheduled to take place in the industrial environment. In another embodiment, system 100 enables obtaining real-time information indicative of human error of at least one employee associated with the task.

System 100 may include at least one sensing device 105 that may (or may not) be associated with employee 110, a server 115 operatively connected to a database 120, and an output unit 125 associated with the industrial environment. The communication between the different system components may be facilitated by communications network 130.

Consistent with the present disclosure, system 100 may analyze data acquired by a plurality of sensing devices 105 to determine a risk score of a task and/or to identify hazards in the industrial environment. The term "sensing device" refers to any device configured to acquire data and transmit data by wired or wireless transmission. In one embodiment, sensing device 105 may include any type of smart device that can acquire data used for deriving safety-related information or real-time information. The term "smart device" means an electronic device that is connected to another device or network via a wireless protocol, such as Bluetooth, NFC, WiFi, 3G, LTE, etc. In one example, sensing device 105 may include an image capturing device, such as a fixed security camera 105A, autonomous robotic devices with cameras, drones with cameras, etc. In another example, sensing device 105 may include a wearable device, such as a smart helmet 105B, smart protective gear, smart glasses, a clip-on camera, etc. In another example, sensing device 105 may include a wireless communication device, such as a worker's handheld communication device 105C, a tablet, a mobile station, a personal digital assistant, a laptop, etc. In another example, sensing device 105 may include an operational technology sensor, such as OT sensor 105D that can measure various process parameters, such as temperature, pressure, flow, etc. In another example, sensing device 105 may include an environmental sensor 105E, such as smoke detector, anemometers, hygrometers, radiation detectors, etc. In another example, sensing device 105 may include a smart work tool, such as a smart driller, smart excavator, etc. In addition, sensing device 105 may be configure to operated manually, remotely, or autonomously.

Sensing device 105 may exchange raw or processed data with server 115 via respective communication links. Server 115 may include one or more servers connected by network 130. In one example, server 115 may be a cloud server that processes data received from one or more sensing devices (e.g., sensing devices 105A-105E) and processes the data to determine a risk score of a task and/or to identify hazards in the industrial environment. Server 115 may also process the received data to determine recommendations for preventing accidents. The term "cloud server" refers to a computer platform that provides services via a network, such as the Internet. In another example, server 115 may be part of an off-line system associated with industrial environment that communicates with sensing device 105 using a wireless local area network (WLAN) or wire connections and can provide similar functionality as a cloud server. When server 115 is a cloud server it may use virtual machines that may not correspond to individual hardware. Specifically, computational and/or storage capabilities may be implemented by allocating appropriate portions of desirable computation/ storage power from a scalable repository, such as a data center or a distributed computing environment. Server 115 may implement the methods described herein using customized hard-wired logic, one or more Application Specific Integrated Circuits (ASICs) or Field Programmable Gate Arrays (FPGAs), firmware and/or program logic which in combination with the computer system cause server 115 to be a special-purpose machine. According to one embodiment, the methods herein are performed by server 115 in response to a processing device executing one or more sequences of one or more instructions contained in a memory device. In some embodiments, the memory device may include operating system programs that perform operating system functions when executed by the processing device. By way of example, the operating system programs may include Microsoft Windows™, Unix™, Linux™, Apple™ operating systems, personal digital assistant (PDA) type operating systems, such as Apple iOS, Google Android, or other types of operating systems.

As depicted in FIG. 1, server 115 may be coupled to one or more physical or virtual storages such as database 120. Server 115 can access database 120 to process data to determine a risk score of a task, the determination occurring through analysis of data obtained from sensing devices 105. Server 115 can also access work procedures of the industrial environment stored in database 120 to determine if an identified situation in the industrial environment deviates from the work procedures. Database 120 may be a volatile or non-volatile, magnetic, semiconductor, tape, optical, removable, non-removable, or other type of storage device or tangible or non-transitory computer-readable medium. Database 120 may also be part of server 115 or separate from server 115. When database 120 is not part of server 115, database 120 and server 115 may exchange data via a communication link. Database 120 may include one or more memory devices that store data and instructions used to perform one or more features of the disclosed embodiments. In one embodiment, database 120 may include any suitable databases, ranging from small databases hosted on a work station to large databases distributed among data centers. Database 120 may also include any combination of one or more databases controlled by memory controller devices (e.g., server(s), etc.) or software, such as document management systems, Microsoft SQL databases, SharePoint databases, Oracle™ databases, Sybase™ databases, or other relational databases.

Consistent with the present disclosure, sensing device 105 and/or server 115 may communicate with output unit 125 to present information derived from processing data acquired by sensing devices 105. For example, output unit 125 may display identified real-time hazards and potential hazards on a personalized map together with visual indicators of the hazard's severity and the hazard's type. In one embodiment, output unit 125 may be part of a factory manager station for controlling and monitoring the safety of a factory. In another embodiment, output unit 125 may be part of an employee station. Output unit 125 may be part of or connected to a desktop computer, a laptop computer, a PDA, a personal communication device, a dedicated terminal, etc. In this embodiment, system 100 may transmit location-based messages to output units 125 of employees located in proximity to a real-time hazard. In one example, the messages displayed on each output unit 125 may include a personalized location-based evacuation map showing the closest emergency exit.

Network 130 facilitates communications and data exchange between sensing device 105, server 115, and output unit 125 when these components are coupled to network 130. In one embodiment, network 130 may be any type of network that provides communications, exchanges information, and/or facilitates the exchange of information between network 130 and different elements of system 100. For example, network 130 may be the Internet, a Local Area Network, a cellular network (e.g., 2G, 2G, 4G, 5G, LTE), a public switched telephone network (PSTN), or other suitable connection(s) that enables system 100 to send and receive information between the components of system 100.

The components and arrangements shown in FIG. 1 are not intended to limit the disclosed embodiments, as the system components used to implement the disclosed processes and features can vary. For example, system 100 may include multiple servers 115, and each server 115 may host a certain type of service, e.g., a first sever that can process data retrieved from database 120 and determine a predicted risk score of a scheduled task, and a second server that can process real-time data received from sensing devices 105 and determine a actual risk score of a task taking place.

Figure 2:
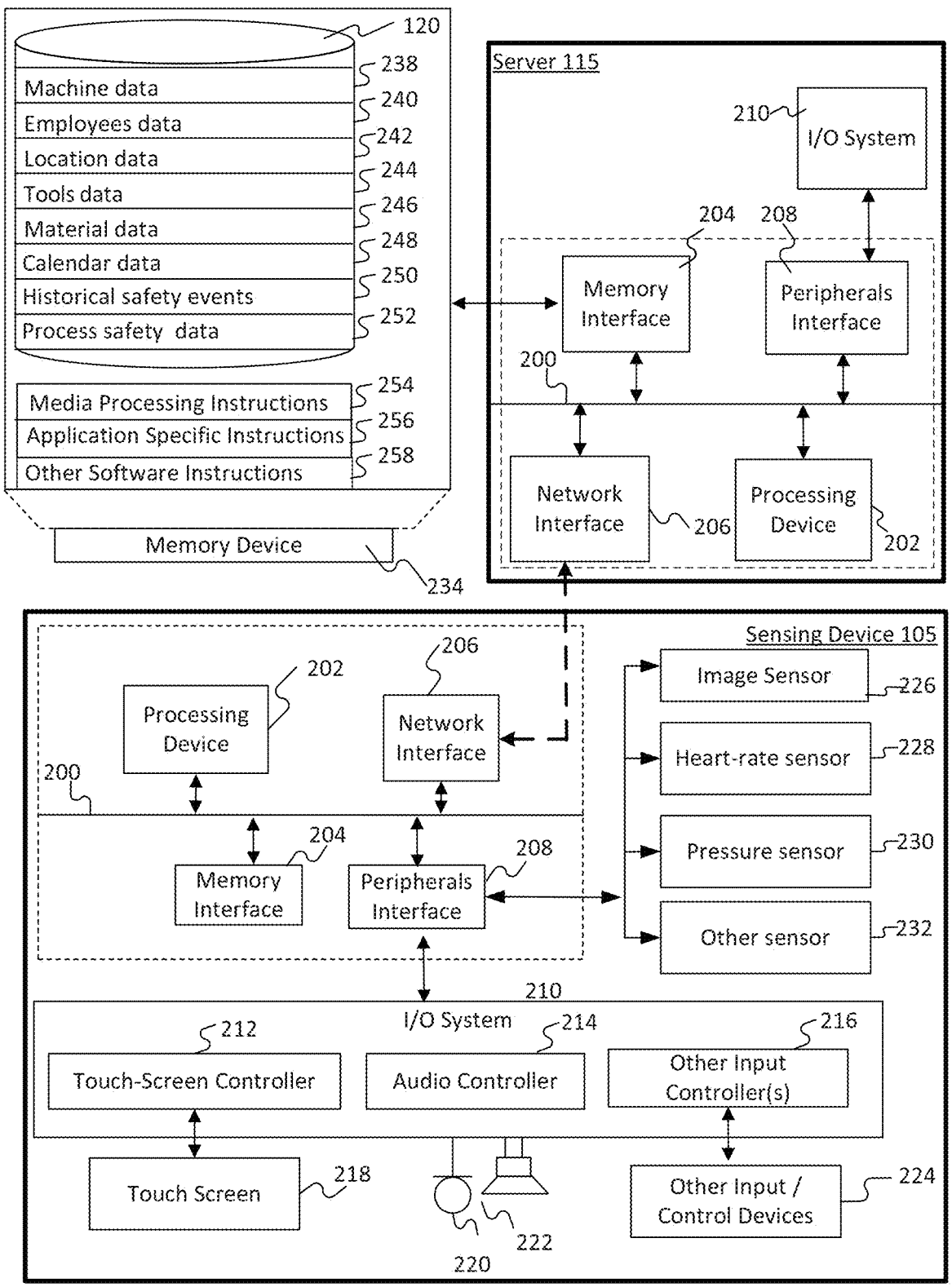
FIG. 2 is a block diagram that illustrates some of the components of the exemplary system, consistent with the present disclosure.

FIG. 2 is a block diagram of example configurations of server 115 and sensing device 105. In one embodiment, both server 115 and sensing device 105 includes a bus 200 (or other communication mechanism) that interconnects subsystems and components for transferring information within server 115 and/or sensing device 105. For example, bus 200 may interconnect a processing device 202, a memory interface 204, a network interface 206, and a peripherals interface 208 connected to I/O system 210.

Processing device 202, shown in FIG. 2, may include at least one processor configured to execute computer programs, applications, methods, processes, or other software to perform embodiments described in the present disclosure. The term "processing device" refers to any physical device having an electric circuit that performs a logic operation. For example, the processing device may include one or more integrated circuits, microchips, microcontrollers, microprocessors, all or part of a central processing unit (CPU), graphics processing unit (GPU), digital signal processor (DSP), field programmable gate array (FPGA), or other circuits suitable for executing instructions or performing logic operations. The processing device may include at least one processor configured to perform functions of the disclosed methods such as a microprocessor manufactured by Intel™ or manufactured by AMD™. The processing device may include a single core or multiple core processors executing parallel processes simultaneously. In one example, the processing device may be a single core processor configured with virtual processing technologies. The processing device may implement virtual machine technologies or other technologies to provide the ability to execute, control, run, manipulate, store, etc., multiple software processes, applications, programs, etc. In another example, the processing device may include a multiple-core processor arrangement (e.g., dual, quad core, etc.) configured to provide parallel processing functionalities to allow a device associated with the processing device to execute multiple processes simultaneously. It is appreciated that other types of processor arrangements could be implemented to provide the capabilities disclosed herein.

In some embodiments, processing device 202 may use memory interface 204 to access data and a software product stored on a memory device or a non-transitory computer-readable medium. For example, server 115 may use memory interface 204 to access database 120. As used herein, a non-transitory computer-readable storage medium refers to any type of physical memory on which information or data readable by at least one processor can be stored. Examples include random access memory (RAM), read-only memory (ROM), volatile memory, nonvolatile memory, hard drives, CD ROMs, DVDs, flash drives, disks, any other optical data storage medium, any physical medium with patterns of holes, a RAM, a PROM, and EPROM, a FLASH-EPROM or any other flash memory, NVRAM, a cache, a register, any other memory chip or cartridge, and networked versions of the same. The terms "memory" and "computer-readable storage medium" may refer to multiple structures, such as a plurality of memories or computer-readable storage mediums located within, server 115, sensing device 105, or at a remote location. Additionally, one or more computer-readable storage mediums can be utilized in implementing a computer-implemented method. The term "computer-readable storage medium" should be understood to include tangible items and exclude carrier waves and transient signals.

Both server 115 and sensing device 105 and may include network interface 206 coupled to bus 200. Network interface 206 may provide a two-way data communication to a local network, such as network 130. In FIG. 2 the communication between server 115 and sensing device 105 is represented by a dashed arrow. In one embodiment, network interface 206 may include an integrated services digital network (ISDN) card, cable modem, satellite modem, or a modem to provide a data communication connection to a corresponding type of telephone line. As another example, network interface 206 may include a local area network (LAN) card to provide a data communication connection to a compatible LAN. In another embodiment, network interface 206 may include an Ethernet port connected to radio frequency receivers and transmitters and/or optical (e.g., infrared) receivers and transmitters. The specific design and implementation of network interface 206 depends on the communications network(s) over which server 115 and sensing device 105 are intended to operate. For example, in some embodiments, sensing device 105 may include network interface 206 designed to operate over a GSM network, a GPRS network, an EDGE network, a Wi-Fi or WiMax network, and a Bluetooth® network. In any such implementation, network interface 206 may be configured to send and receive electrical, electromagnetic or optical signals that carry digital data streams representing various types of information.

Both server 115 and sensing device 105 may also include peripherals interface 208 coupled to bus 200. Peripherals interface 208 be connected additional components or subsystems to facilitate multiple functionalities. In one embodiment, peripherals interface 208 may be connected to I/O system 210 configured to receive signals or input from devices and providing signals or output to one or more devices that allow data to be received and/or transmitted by server 115 and sensing device 105. In one example, I/O system 210 may include a touch screen controller 212, audio controller 214, and/or other input controller(s) 216. Touch screen controller 212 may be coupled to a touch screen 218. Touch screen 218 and touch screen controller 212 can, for example, detect contact, movement or break thereof using any of a plurality of touch sensitivity technologies, including but not limited to capacitive, resistive, infrared, and surface acoustic wave technologies as well as other proximity sensor arrays or other elements for determining one or more points of contact with the touch screen 218. Touch screen 218 can also, for example, be used to implement virtual or soft buttons and/or a keyboard. While a touch screen 218 is shown in FIG. 2, I/O system 210 may include a display screen (e.g., CRT or LCD) in place of touch screen 218. Audio controller 214 may be coupled to a microphone 220 and a speaker 222 to facilitate voice-enabled functions, such as voice recognition, voice replication, digital recording, and telephony functions. The other input controller(s) 216 may be coupled to other input/control devices 224, such as one or more buttons, rocker switches, thumb-wheel, infrared port, USB port, and/or a pointer device such as a stylus.

With regards to sensing device 105 peripherals interface 208 may also be connected to different sensors. In one example, fixed security camera 105A and worker's handheld communication device 105C may include an image sensor 226 for capturing image data. The term "image sensor" refers to a device capable of detecting and converting optical signals in the near-infrared, infrared, visible, and ultraviolet spectrums into electrical signals. The electrical signals may be used to form an image or a video stream (i.e. image data) based on the detected signal. The term "image data" includes any form of data retrieved from optical signals in the near-infrared, infrared, visible, and ultraviolet spectrums. Examples of image sensors may include semiconductor charge-coupled devices (CCD), active pixel sensors in complementary metal-oxide-semiconductor (CMOS), or N-type metal-oxide-semiconductor (NMOS, Live MOS). In another example, smart helmet 105B may include a heart-rate sensor 228 for capturing an employee heart rate. In another example, OT sensor 105D may include a pressure sensor 230 that can measure a status of a machine in the factory. Other sensing devices may have other sensors connected to the peripherals interface 208 to facilitate related functionalities. In addition, a GPS receiver can also be integrated with, or connected to, sensing device 105.

Consistent with the present disclosure, server 115 may use memory interface 204 to access memory device 234. Memory device 234 may include high-speed random access memory and/or non-volatile memory such as one or more magnetic disk storage devices, one or more optical storage devices, and/or flash memory (e.g., NAND, NOR). In some embodiments, memory device 234 may be included in, for example, server 115. Alternatively or additionally, memory 234 may be stored in an external storage device communicatively coupled with server 115, such that one or more database (e.g., database 120) may be accessible over network 130. Further, in other embodiments, the components of memory device 234 may be distributed in more than one server.

In the illustrated example depicted in FIG. 2, memory device 234 hosts database 120. Consistent with embodiments of the present disclosure, database 120 may include data about the main five factors that generate a safe work environment. Specifically, database 120 includes machine data 238 (e.g., indications of the operational statuses of machines in in the industrial environment, such as scheduled repairs, maintenance requirements, and more)), employees data 240 (e.g., attendance data, records of training provided, evaluation and other performance-related communications, productivity information, qualifications, permits, previous safety events, and more), location data 242 (e.g., indications of areas in the industrial environment associated with certain safety restrictions and locations of specific safety-related features, such as the locations of fire extinguisher, electrical cabinet, and more), tools data 244 (e.g., indications of the operational statuses of each tool, a list of employees permitted to operate each tool, indications of the location of each tool, and more), material data 246 (e.g., indications of the storage statuses of machines in in the industrial environment, such as current temperature, transportation schedule, and more), calendar data 248 (e.g., holidays, national days, and more), historical safety events 250, and process safety data 252 (e.g., infrastructure blueprints, machinery inventory, material inventory, regulations about, for example, using and maintaining specific machines, a risk analysis plan, locations of known hazards, recommendations and/or restrictions associated with areas in the industrial environment, work procedures data that may stem from federal, state and local regulations, as well as from private initiatives such as total quality management and voluntary protection programs).

Consistent with the present disclosure, memory device 234 may also include media processing instructions 256 to facilitate media processing-related processes and functions, and/or other software instructions 258 to facilitate other processes and functions. Memory device 234 may also include application specific instructions 260 to facilitate a process for preventing an accident. An example process is described below with reference to FIG. 5. Memory device 234 may also include application specific instructions or modules to facilitate different processes for preventing accidents in the industrial environment. Example application specific modules are described below with reference to FIG. 3. In other embodiments of the disclosure, memory device 234 may store additional types of data or fewer types of data. Furthermore, various types of data may be stored in one or more other memory devices.

Figure 3:
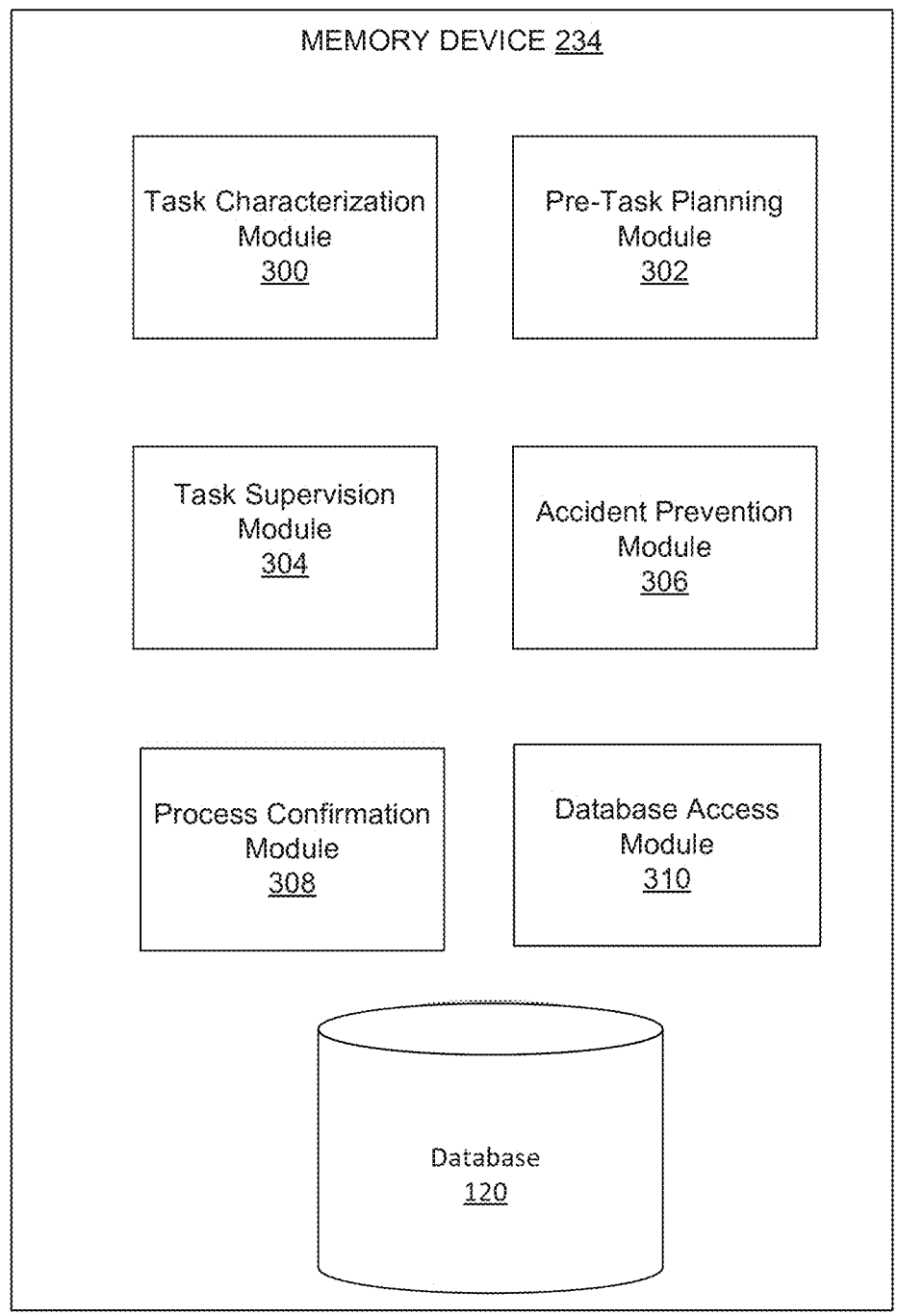
FIG. 3 is a block diagram that illustrates an exemplary embodiment of a memory containing software modules, consistent with the present disclosure.

FIG. 3 illustrates an exemplary embodiment of a memory 234 containing software modules consistent with the present disclosure. In particular, as shown, memory 234 may include a task characterization module 300, a pre-task planning module 302, a task supervision module 304, an accident prevention module 306, a process confirmation module 308, and a database access module 310. Modules 300, 302, 304, 306, 308 and 310 may contain software instructions for execution by at least one processing device, e.g., processing device 202. Consistent with the present disclosure, task characterization module 300, pre-task planning module 302, task supervision module 304, accident prevention module 306, process confirmation module 308, database access module 310, and database 120 may cooperate to perform multiple operations. For example, task characterization module 300, pre-task planning module 302, task supervision module 304, accident prevention module 306, and process confirmation module 308 may be used to eliminate risk for personal and process work accidents on three levels:

Behavioral level—system 100 may eliminate risk from unforeseen dynamic risks by enforcing safe behavior even when workers do not see any indication that they may be in immediate risk (e.g., ladder stability, gasses and fumes, electricity, and more).

Non-isolated pre-task planning—system 100 may eliminate risks that can be known by expanding the analysis to other worker activities, worker conditions, work environments, and temporal changes. For example, system 100 may make workers and managers aware of the extended risks associated with outside factors (e.g., other tasks) to enable planning a scheduled task in a safe manner.

Real-time intervention—system 100 may detect that a change to the operating environment or a control indicator is not as expected (e.g., machine operational status, weather, other tasks, worker specific risk profile) or a combination of factors creates a risk score that is unacceptable. Thereafter, system 100 may initiate a remedial action, such as triggering real-time alerts, preventing the task from being performed by shutting down connected machines, or making the task paused or locked.

In one embodiment, task characterization module 300 may determine at least one characteristic of a task based on received details and historical safety-related information. Pre-task planning module 302 may determine that a predicted risk score of the scheduled task is below a first threshold, which means the task has a green light. Task supervision module 304 may use real-time information to determine that an actual risk score of the task has changed from the predicted risk score. For example, that the actual risk score is higher than the predicted risk score. Accident prevention module 306 may determine which appropriate remedial action is needed for preventing an accident, and initiate the remedial action. Process confirmation module 308 may use information collected during task execution and confirm that the design integrity, the operational integrity, and the technology integrity comply with work process procedures. Database access module 310 may interact with database 120, which may store safety-related information and work procedures of the industrial environment and any other information associated with the functions of modules 300-310.

Figure 4A:
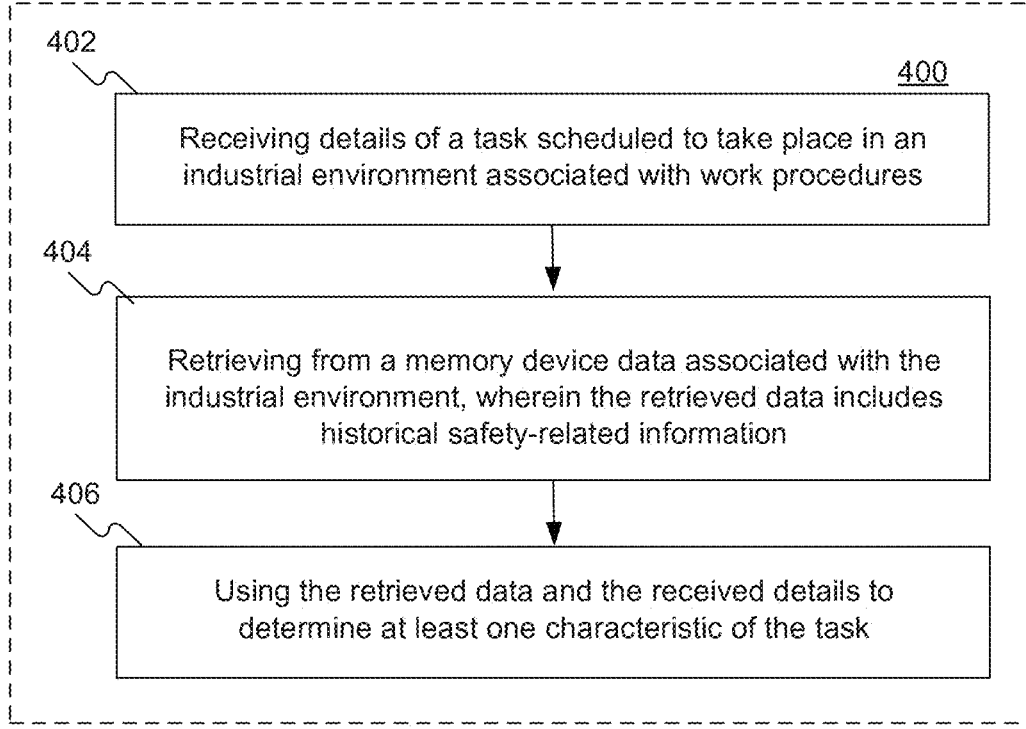
FIGS. 4A-4E are flowcharts of exemplary methods associated with the software modules of FIG. 3, consistent with the present disclosure.

Reference is now made to FIG. 4A, which depicts an example method 400 that may be executed by task characterization module 300, consistent with the present disclosure. In one embodiment, all of the steps of method 400 may be performed by components of system 100. It will be appreciated, however, that other implementations are possible and that other components may be utilized to implement method 400. It will be readily appreciated that the illustrated method can be altered to modify the order of steps, delete steps, or further include additional steps.

At step 402, a processing device (e.g., processing device 202) may receive details of a task scheduled to take place in an industrial environment associated with work procedures. In one embodiment, the details of the task may be received by a network interface (e.g., network interface 206). At step 404, the processing device may retrieve from a memory device (e.g., memory device 234) data associated with the industrial environment. The retrieved data includes historical safety-related information (e.g., historical safety events 250). At step 404, the processing device may use the retrieved data and the received details to determine at least one characteristic of the task. Consistent with the present disclosure, the at least one characteristic of the task may include at least one of: estimated start time of the task, identity of employees expected to participate in the task, expected time duration of the task, type of tools expected to be used in the task, type of material expected to be used in the task, potential accidents associated with the task, potential accidents associated with the identity of employees.

At step 406, the processing device may use the retrieved data and the received details to determine at least one characteristic of the task. In one embodiment, the at least one characteristic of the task may relate to the properties of the task, such as work in confined space, work in height, or hot work. In another embodiment, the at least one characteristic of the task may relate to special environmental properties such as chemical, bio hazard, radiation, pollution etc. The at least one characteristic of the task may be indicative of the type of physical or mental effort needed to complete the task. In addition, the task may be also be characterized by association with relation to other tasks taking place in the same or relevant proximity area or time. For example, another worker performing a task in height which changes the properties of the task of a worker on a lower level and who is exposed to a potentially falling object from above. In other examples, the task may also be characterized by it being done as part of a workplace routine or out of routine which may be unexpected to other people. In some cases, the task may also be characterized as its ability to spot leading indicators for a potential malfunction or crisis.

Figure 4B:
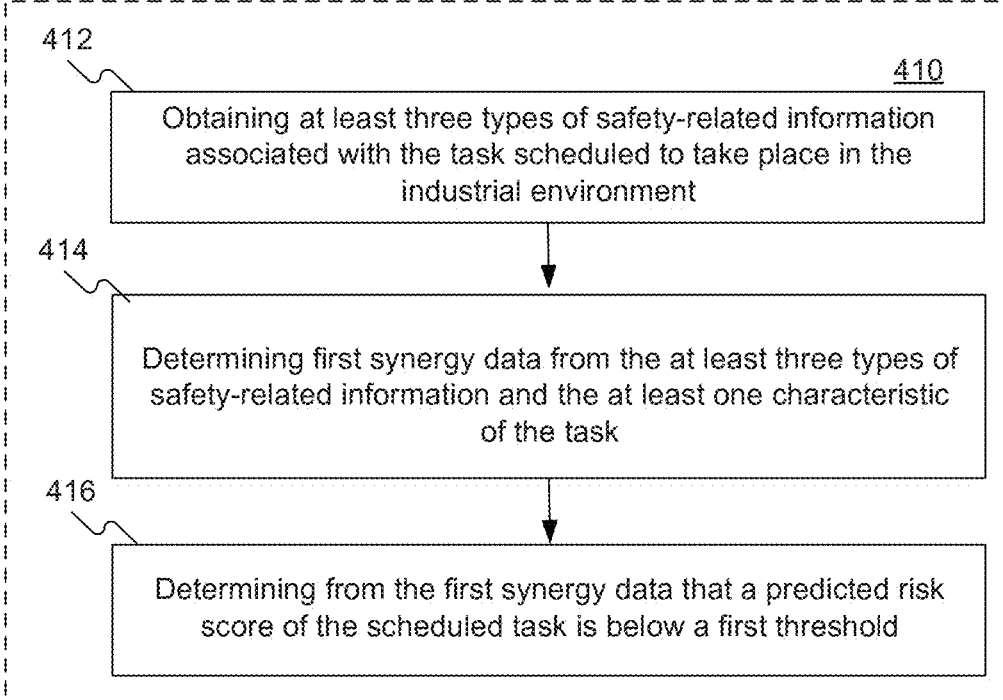

Reference is now made to FIG. 4B, which depicts an example method 410 that may be executed by pre-task planning module 302, consistent with the present disclosure. Similar to method 400, the steps of method 410 may be performed by components of system 100 and method 410 can be altered to modify the order of steps, delete steps, or further include additional steps.

At step 412, the processing device may obtain at least three types of safety-related information associated with the task scheduled to take place in the industrial environment. In some embodiments, the processing device may obtain and use at least two types of safety-related information, and in others at least four types of safety-related information. Consistent with one embodiment of the disclosure, the safety-related information may include information about each worker assigned to the task. Specifically, the worker performance may not be consistent and system 100 can account and predict for different causes for changed in the worker performance. For example, the level of concentration of the worker may vary when just starting a task versus after repeating it many times. Also people perform differently when they are just starting a shift versus when they want to finish a task and rush to go home. In addition, system 100 may consider impact of repetitive or sustained force, sustained or awkward posture, exposure to vibration or noise, restrictive movement space or clothing, restricted sensory perception, and more. System 100 may also determine if a worker may be tired, ill, under a restrictive diet or medication, under emotional stress, suffering from allergies, or just not accustomed to the task or environment such as the weather condition. In another embodiment, the safety-related information may include information about location of the task. Specifically, the location has many characteristics and system 100 can consider the restrictions associated with the planned locations of the scheduled task. For example, the location information may include: area classification (class, zone), symbol for equipment classification, type of protection designations, gas identification group, temperature classification, ignition sources, and more. In another embodiment, the safety-related information may include information about the tools expected to be used in the task. Specifically, in many cases the way and how recently a tool or object was used may change the risk it presents to the worker and to the task quality. For example, the information about the tools may include an indication that a certain tool has overheated due to previous use, thus may still be a possible and unmitigated ignition source or alternatively a source for burns and injury; an indication that a tool may be equipped with incompatible or damaged fittings or connected to a power source other than expected; an indication that a tool may fall to a lower level; an indication that a tool also may be inappropriate to be operated with using the designated Personal Protective Equipment (PPE). In another embodiment the safety-related information may include information about materials expected to be used in the task. Specifically, different materials have different requirements for handling and for transporting, while some materials may change with time. The information may include details on materials that may evaporate, pressured by container changes, biomass gasses produced, radiation, and more. The information about materials expected to be used in the task may include details on the material, such as, measurements, expiration date, temperature restrictions, and more. In another embodiment the safety-related information may include information about the estimated start time of the task. Specifically, different temporal cycles may have different effect on the predicted risk score. For example, the information about the estimated start time of the task may include indications on the type of shift (day or night), time within a shift (start, mid or end), time of the day (even as it relates to light level or sun direction/visibility), time of high activity by other workers or lone worker.

At step 414 the processing device may determine first synergy data from the at least three types of safety-related information and the at least one characteristic of the task. In one embodiment, the first synergy data may include details of at least one handover event expected to happen while the task is taking place. As mentioned above, the handover event may be an employee shift change during the task, a material change during the task, a tool change during the task, a supervisor change during the task, and a change from working during day time and night time. For example, the system may detect that during the task two of the workers are expected to be replaced (e.g., it is the end of their shift), this change will increase the risk score of the scheduled task. In another embodiment, the first synergy data may include details about a status change event associated with an asset of the retail environment. In one example, a status change event can happen when a machine goes back into service after being maintained or repaired. In another example, a status change event can happen when a day-shift employee is assigned to a night shift.

At step 416 the processing device may determine from the first synergy data that a predicted risk score of the scheduled task is below a first threshold. Consistent with the present embodiment, system 100 may determine the value of the risk score using the safety-related information, a plurality of rules, and a plurality of factors. The plurality of rules may include industry specific machine learning derived rules, location rules, worker risk analysis rules, policy rules, best practice rules, regulation rules, and more. The plurality of factors may include industry task risk analysis factors, environmental factors, timing factors, environmental risk factors, task statistics factors, and more. In some embodiments, pre-task planning module 302 may determine the value of the risk score using past data, industry statistics, and operational parameters to predict the likely range of parameters that are likely to be present. For example, pre-task planning module 302 may predict the systematic and specific risk for each task at the planned time, place, worker, and activity scenarios. In one embodiment, for each scenario or task the pre-task planning module 302 may generate a risk score as well as a combined risk score with conjunction to other planned tasks in time or space proximity.

In some embodiments, pre-task planning module 302 may further includes instructions for causing the processing device to provide an employee associated with the task with pre-task planning information. For example, the employee may be a worker assigned to the task and the pre-task planning information includes personalized training based on past safety incidents included in the historical safety-related information; recommendations on how to execute the task according to the work procedures; information on existing hazards located in an area associated with the task; and information on potential hazards located in an area associated with the task. Alternatively, the employee may be a manager assigned to supervise the task and the pre-task planning information includes details about the task, such as the names and phone numbers of the workers that are assigned to the task.

Figure 4C:
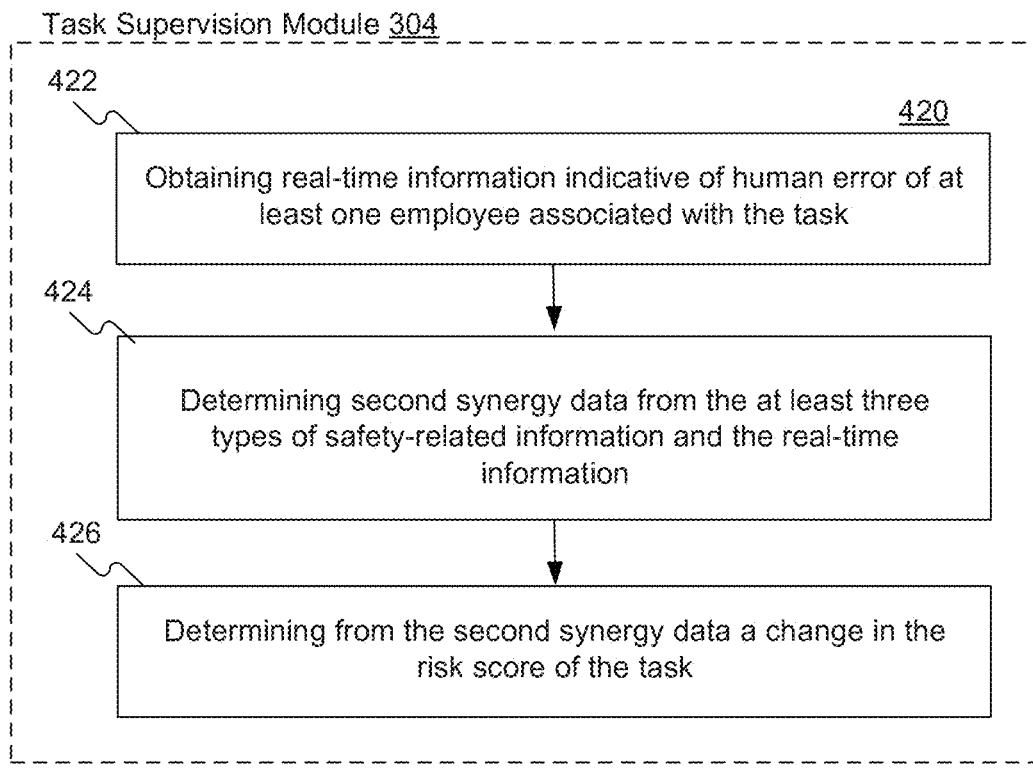

Reference is now made to FIG. 4C, which depicts an example method 420 that may be executed by task supervision module 304, consistent with the present disclosure. Similar to method 400, the steps of method 420 may be performed by components of system 100 and method 420 can be altered to modify the order of steps, delete steps, or further include additional steps.

At step 422, the processing device may obtain real-time information indicative of human error of at least one employee associated with the task. The real-time information may be obtained from at least one of: a plurality of cameras located in the industrial environment, one or ore communication devices of employees in the industrial environment, wearable sensors of employees in the industrial environment, operational technology (OT) sensors, environmental sensors, and sensors associated with working tools. In one embodiment the real-time information may include at least one, at least two, or at least three of: detected changes in the performances of an employee assigned to the task, detected changes in planned locations of the task, detected changes in tools expected to be used in the task, detected changes in materials expected to be used in the task, detected changes in an expected start time of the task, detected changes in an expected weather during the task, and detected deviation from the process safety procedures.

At step 424, the processing device may determine second synergy data from the at least three types of safety-related information and the real-time information. In one embodiment, the second synergy data may include details on a situation in the industrial environment that deviates from work procedures of the industrial environment. Example situations that deviate from normal operations work procedures may include times where there are training simulations or audits that divert workers and attention from normal activity. Other example situations may include times of extreme conditions, such as, natural extreme conditions (e.g., snow or storm or heat) personal work-related conditions (e.g., strike or social unrest). Other example situations may include changes in the work environment, such as renovation or maintenance taking place. In another embodiment the second synergy data may include details on a situation not caused by workers assigned to the task but still have a direct effect on the safety of the task. In a first example, the second synergy data may include identifying a vehicle transporting evaporating flammable materials that drives through an area where the task is executed. In a second example, the second synergy data may include identifying a change in weather conditions that may have an effect on the worker's performances (e.g., rain might change surface properties, making them slippery or create electricity hazards, dust and wind storms might impair workers' visibility and cause a worker to fall on the same level or to a lower level, strong wind might cause objects from levels above to come loose and fall or hit other objects or workers.) In a third example, the second synergy data may include identifying the movements of large vehicles and/or vehicles carrying unstable or extruding load in the area of the task.

At step 426, the processing device may determine from the second synergy data that an actual risk score of the task has changed from the predicted risk score. In one embodiment, the change in the risk score may be a decrease of the risk score due to the real-time event, which may trigger initiating a remedial action. In one example, a task of fixing a light pole in the industrial environment has received a risk score of 3.8 partially because there was rain prediction during the execution of the task. If system 100 detects that it does not rain during the task, it may decrease the risk score to 3.4. When the actual risk score is lower than the predicted risk score, the remedial action may include removing one or more measures or restrictions associated with the task. In one case, with reference to the example above, for tasks with a risk score higher than 3.5 remote supervision may be required but since the actual risk score is now lower than the threshold, system 100 may cancel the requirement of the remote supervision. In another case, also reference to the example above, when it is not raining, system 100 may inform the workers assigned to the task that they may use a ladder and not only a bucket truck. In another embodiment, the change in the risk score may also be an increase of the risk score due to the real-time event, which may trigger initiating a remedial action. One of the causes for an increase in the risk score may be detection of an event indicative of deviation from work procedures of the industrial environment. Different examples of remedial actions triggered when the change in the risk score is an increase of the risk score are discussed in greater details below.

Figure 4D:
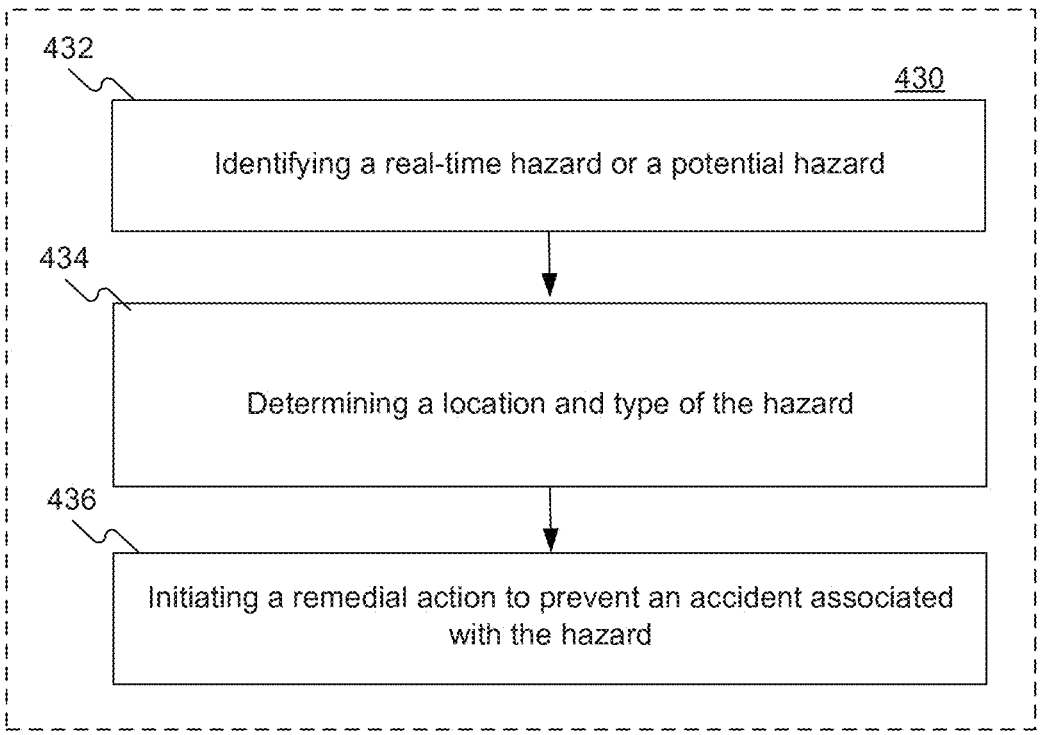

Reference is now made to FIG. 4D, which depicts an exemplary method 430 that may be executed by accident prevention module 306, consistent with the present disclosure. Method 430 may be executed when the actual risk score of the task is above a certain threshold. Similar to method 400, the steps of method 430 may be performed by components of system 100 and method 430 can be altered to modify the order of steps, delete steps, or include further additional steps.

At step 432, the processing device may identify a real-time hazard and/or a potential hazard. The term "real-time hazard" refers to a cause of immediate danger associated with a place, a machine, a material, or a tool. Consistent with the present disclosure real-time hazards may have a personal safety source. In other words, a real-time hazard may be caused by a direct human action. In one example, a real-time hazard happen when a worker raises the heat in a machine above an auto ignition level for a chemical in proximity to the machine. In addition, ill maintained equipment and changing environment conditions may cause workers to improvise and not to perform as they should. These factors may cause personal accident while workers attempt to complete the task. For example, when the working environment is much hotter than usual, it may cause the eye protection glasses impossible to see through, so worker removes and is being exposed to danger. The term "potential hazard" refers to a cause of future danger associated with a place, a machine, a material, or a tool. Consistent with the present disclosure potential hazards may have a process safety source. In other words, a potential hazard may be caused by unplanned or unexpected deviations in process conditions. An example of a potential hazard happened when the structural integrity of a shipping container deteriorate and can cause a toxic waste leakage.

At step 434, the processing device may determine a location and a type of hazard. To determine the location of the hazard, system 100 may use any form of location tracking technology or locating method: location information manually inputted by a worker; WiFi server location data; Bluetooth based location data; any form of Global Positions Systems (e.g., GPS accessed using Bluetooth or GPS accessed using any form of wireless and/or non-wireless communication); any form of network based triangulation (e.g., WiFi server information based triangulation, Bluetooth server information based triangulation; cell identification based triangulation, enhanced cell identification based triangulation, uplink-time difference of arrival (U-TDOA) based triangulation, time of arrival based triangulation, angle of arrival based triangulation); any form of systems using a geographic coordinate system (e.g., longitudinal and latitudinal based, geodesic height based, Cartesian coordinates based); any form of radio frequency identification systems (e.g., long range RFID, short range RFID; active RFID tags, passive RFID tags, battery assisted passive RFID tags). To determine the type of the hazard, system 100 may use artificial intelligence (AI) and machine learning algorithms. The types of the hazards may include electrical hazards (e.g., frayed cords, missing ground pins, and improper wiring); machinery-related hazards (e.g., exposed moving machinery parts, and safety guards removed); tripping hazards (e.g., cords running across the floor, and wet floor); height-related hazards (e.g., unsafe ladders, scaffolds, roofs, and any raised work area); biological hazards (e.g., fungi/mold, insect bites, animal and bird droppings); physical hazards (e.g., exposure to radiation, extreme temperatures, and noise); chemical hazards (e.g., spilled liquids, exposure to toxic fumes, explosive chemicals not stored properly, and more). The present disclosure is not limited to the listed-above types of hazards, additional types or different categorizations are encompassed in this disclosure.

At step 436, the processing device may initiate a remedial action to prevent an accident associated with the detected hazard. Consistent with the present disclosure, the remedial action may prevent of a series of incidents associated with personal safety or a catastrophic incident associated with process safety. In one embodiment, initiating the remedial action may include identifying an employee that is responsible for handling the determined type of hazard; and transmitting a message to the identifying employee, wherein the message may include the location of the hazard (e.g., the message may include an indication of the actual risk score and the GPS location of the hazard). In another embodiment, initiating the remedial action may include identifying an employee located within a distance of the hazard, wherein the distance is determined based on type of the hazard (e.g., for gas leakage the distance may be greater than wet floor). Thereafter, system 100 may transmit a location-based warning to the identified employee. In another embodiment, initiating the remedial action may include identifying an employee located within a distance of the hazard, and transmitting a personalized location-based evacuation map to the identified employee (e.g., the personalized location-based evacuation map may provide guidance to the closest exit). In another embodiment, initiating the remedial action may include identifying an employee located within a distance of the hazard, and transmitting instructions on how to fix or avoid the hazard to the identified employee (e.g., the instructions may be according to the work procedures of the industrial environment). In other embodiments, initiating the remedial action may include displaying detected hazards on a personalized map together with a visual indicator of the hazard's severity, performing an automatic shutdown to prevent predicted injuries or damages, or creating a customized inspection tour based on detected locations of a plurality of potential hazards and real-time hazards.

Figure 4E:
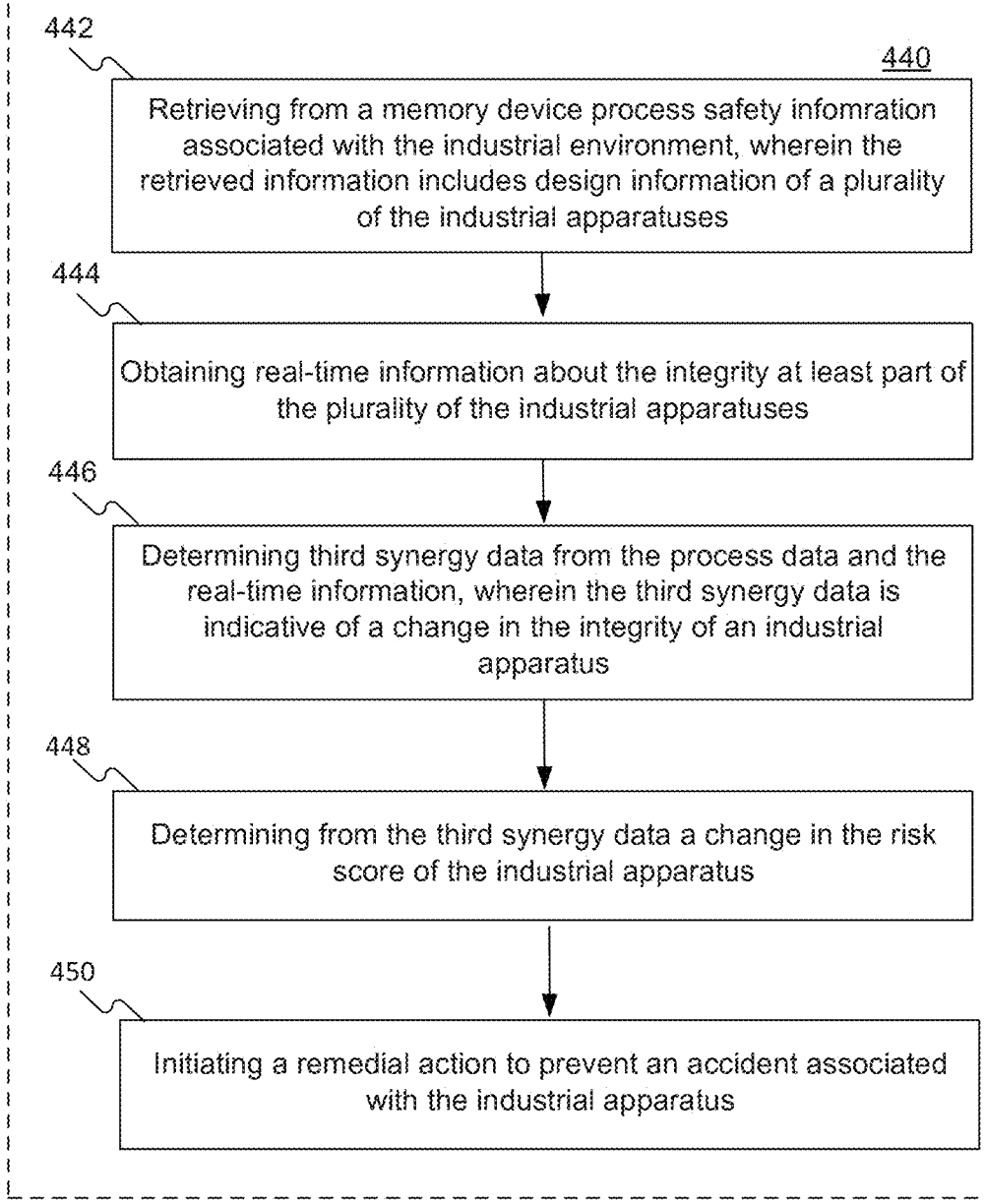

Reference is now made to FIG. 4E, which depicts an example method 440 that may be executed by process confirmation module 308, consistent with the present disclosure. Similar to method 400, the steps of method 440 may be performed by components of system 100 and method 440 can be altered to modify the order of steps, delete steps, or further include additional steps.

At step 442, the processing device may retrieving from a memory device (e.g., database 120) process safety information (e.g., process safety data 252) associated with the industrial environment. In one embodiment, the retrieved information may include design information of a plurality of the industrial apparatuses. As mentioned above, the industrial apparatuses may include machines, structures, facilities found in the industrial environment.

At step 444, the processing device may obtain real-time information about the integrity of at least part of the plurality of the industrial apparatuses. The real-time information may be obtained from at least one of: a plurality of cameras located in the industrial environment, one or more communication devices of employees in the industrial environment, wearable sensors of employees in the industrial environment, operational technology (OT) sensors, environmental sensors, and sensors associated with working tools. The real-time information may include indications of employees actions that deviate from the process safety procedures.

At step 446, the processing device may determine third synergy data from the process data and the real-time information. In one embodiment, the third synergy data is indicative of a change in the integrity of an industrial apparatus. For example, the change in the integrity of an industrial apparatus may include at least one change in the design integrity, the operational integrity, and the technology integrity.

At step 448, the processing device may determine from the third synergy data a change in the risk score of the industrial apparatus. In one embodiment, the change in the risk score may be an increase of the risk score due to the real-time event, which may trigger initiating a remedial action. In one example, a risk score of silo may increase when the system detects a corrosion in one of the pipes entering to the silo.

At step 450, the processing device may initiate a remedial action to prevent an accident associated with the industrial apparatus. In one embodiment, initiating the remedial action may include identifying an employee that is responsible for industrial apparatus; and transmitting a message to the identifying employee, wherein the message may include the status of the industrial apparatus. In another embodiment, initiating the remedial action may include identifying an employee located within a distance of the industrial apparatus, wherein the distance is determined based on type of the hazard associated with the industrial apparatus (e.g., for gas leakage the distance may be greater than wet floor). Thereafter, system 100 may transmit a location-based warning to the identified employee. In another embodiment, initiating the remedial action may include identifying an employee located within a distance from the industrial apparatus, and transmitting a personalized location-based evacuation map to the identified employee (e.g., the personalized location-based evacuation map may provide guidance to the closest exit). In another embodiment, initiating the remedial action may include identifying an employee located within a distance from the industrial apparatus, and transmitting instructions on how to fix or avoid the industrial apparatus to the identified employee (e.g., the instructions may be according to the work procedures of the industrial environment). In other embodiments, initiating the remedial action may include performing an automatic shutdown of the industrial apparatus to prevent predicted injuries or damages, or creating a customized inspection tour based on determined risk of the industrial apparatus.

Figure 5:
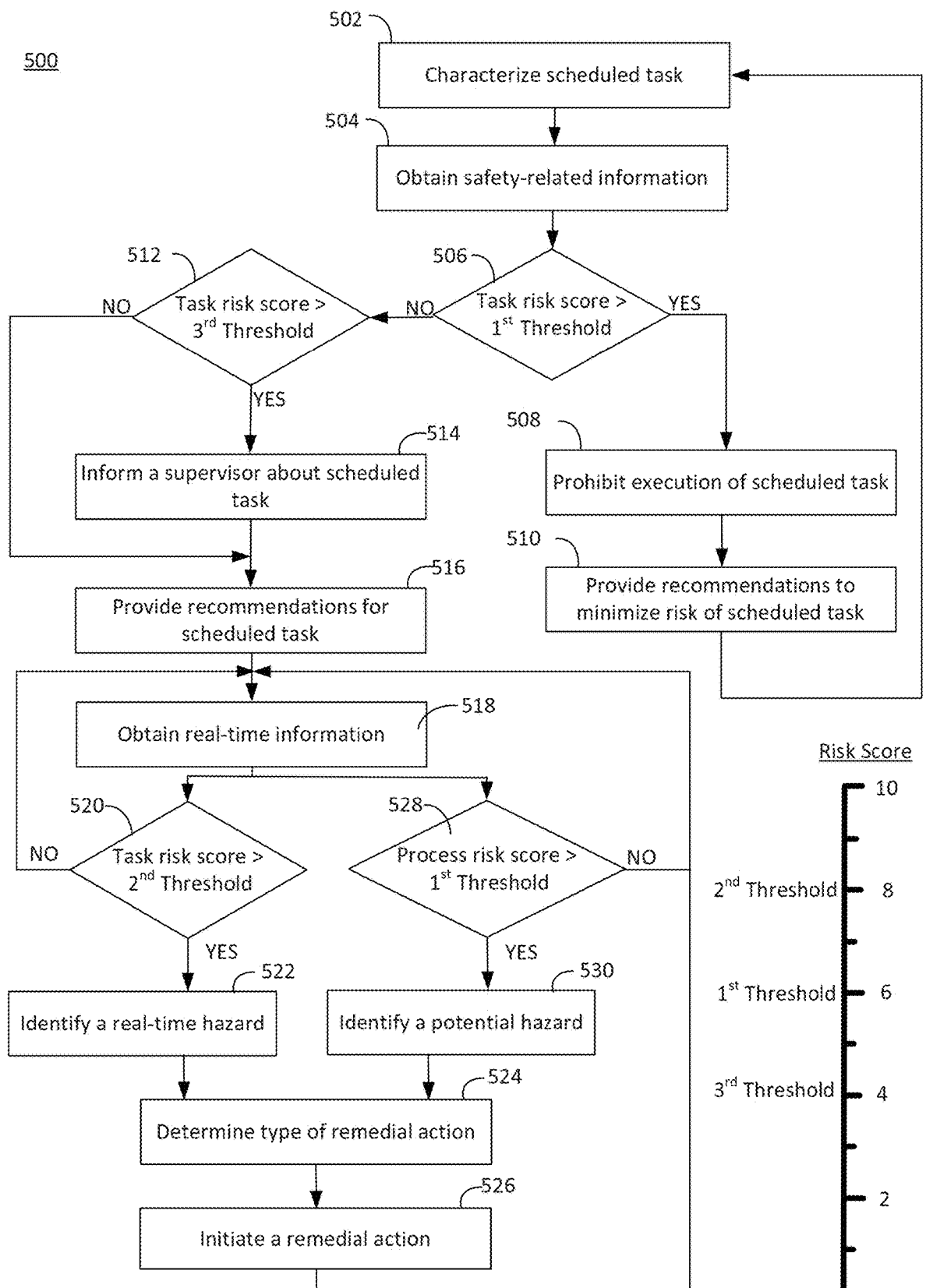
FIG. 5 is a flowchart of an example process used by the exemplary system to prevent an accident in an industrial environment.

FIG. 5 depicts a flowchart of an example process 500 executed by a processing device of system 100 (e.g., processing device 202) for preventing a work accident, according to some embodiments. Process 500 includes comparing the risk score to three different thresholds. The term "threshold" is used here to denote a reference value, a level, a point, or a range of values, for which when the calculated risk score is above it the processing device may follow a first course of action and when the calculated risk score is under it the processing device follows a second course of action. The value of each of the thresholds may be predetermined for each industrial environment or dynamically selected based on the task. An example risk scale with exemplary thresholds is also depicted in FIG. 5. Additional details about specific steps of process 500 are described above.

The process begins when the processing device characterizes a scheduled task (block 502). Thereafter, the processing device may obtain safety-related information (block 504) and use the safety-related information and the task characteristic to determine if a task risk score of the scheduled task is above a first threshold (decision block 506). When the task risk score of the scheduled task is above the first threshold, the processing device may issue a notice prohibiting the execution of the scheduled task (block 508) and provide recommendations to minimize the risk of the scheduled task (block 510). Thereafter, the process may continue when the processing device re-characterizes the task to check if any of the recommendations were implemented and the task risk score of the scheduled task is below the first threshold.

When the task risk score of the scheduled task is below the first threshold, the processing device determines if the task risk score of the scheduled task is above a third threshold (decision block 512). When the task risk score of the scheduled task is above the third threshold, the processing device may issue inform a supervisor about the scheduled task (block 514). Specifically, when the predicted task risk score of the scheduled task is below the first predetermined threshold and above the third predetermined threshold, the method may include informing one or more individuals that a risky task is about to take place. Process 500 continues when the processing device provides recommendations for a scheduled task (block 516). In one embodiment, the recommendations for a scheduled task may include checklists, relevant warnings, suggested tools, and more. In one example, the recommendations for scheduled task may include a safety exam that employees assigned to the task are required to complete. The process continues when the task actually starts, as the processing device obtains real-time information (block 518). The real-time information may be indicative of personal safety issues (e.g., the employee's actions) and also may be indicative of process safety issues (e.g., a change in a machine condition).

After obtaining the real-time information, process 500 splits to two paths that later converge. In the first path, the processing device determines if the actual task risk score is above a second threshold (decision block 520). As long as the actual task risk score is below the second threshold, the process continues with obtaining additional real-time information and monitoring the actual task risk score. When the task risk score is above the second threshold, the processing device may identify a real-time hazard (block 522), determine the type of remedial action needed based on the identified type of hazard (block 524), and initiate a remedial action to prevent an accident from happening (block 526). In the second path, the processing device determines if the process risk score is above the first threshold (decision block 528). In this context, the first threshold represents a level of risk that above it the system will prohibit execution of specific tasks. The actual value of the first threshold may differ from task risk scores and process risk scores. As long as the process risk score is below the first threshold, the process continues with obtaining additional real-time information and monitoring the process risk score. When the process score is above the first threshold, the processing device may identify a potential hazard (block 530), and initiate a remedial action to prevent an accident from happening (block 526). Consistent with the present disclosure, the system may initiate different actions when the identified hazard is associated with personal safety and when the identified hazard is associated with process safety.

Consistent with some embodiments, process 500 discloses a specific method for determining if a risk score associated with a task is above different thresholds. However, a person of ordinary skill in the art would recognize that process 500 may be easily adapted to identify when a risk score of an ongoing task departs from an acceptable range of risk scores associated with the characteristic of the task. Therefore, it will be readily appreciated that the process illustrated in FIG. 5 can be altered to modify the order of steps, delete steps, or further include additional steps. For example, the order of decision block 506 and decision block 512 may be switched.

Figure 6A:
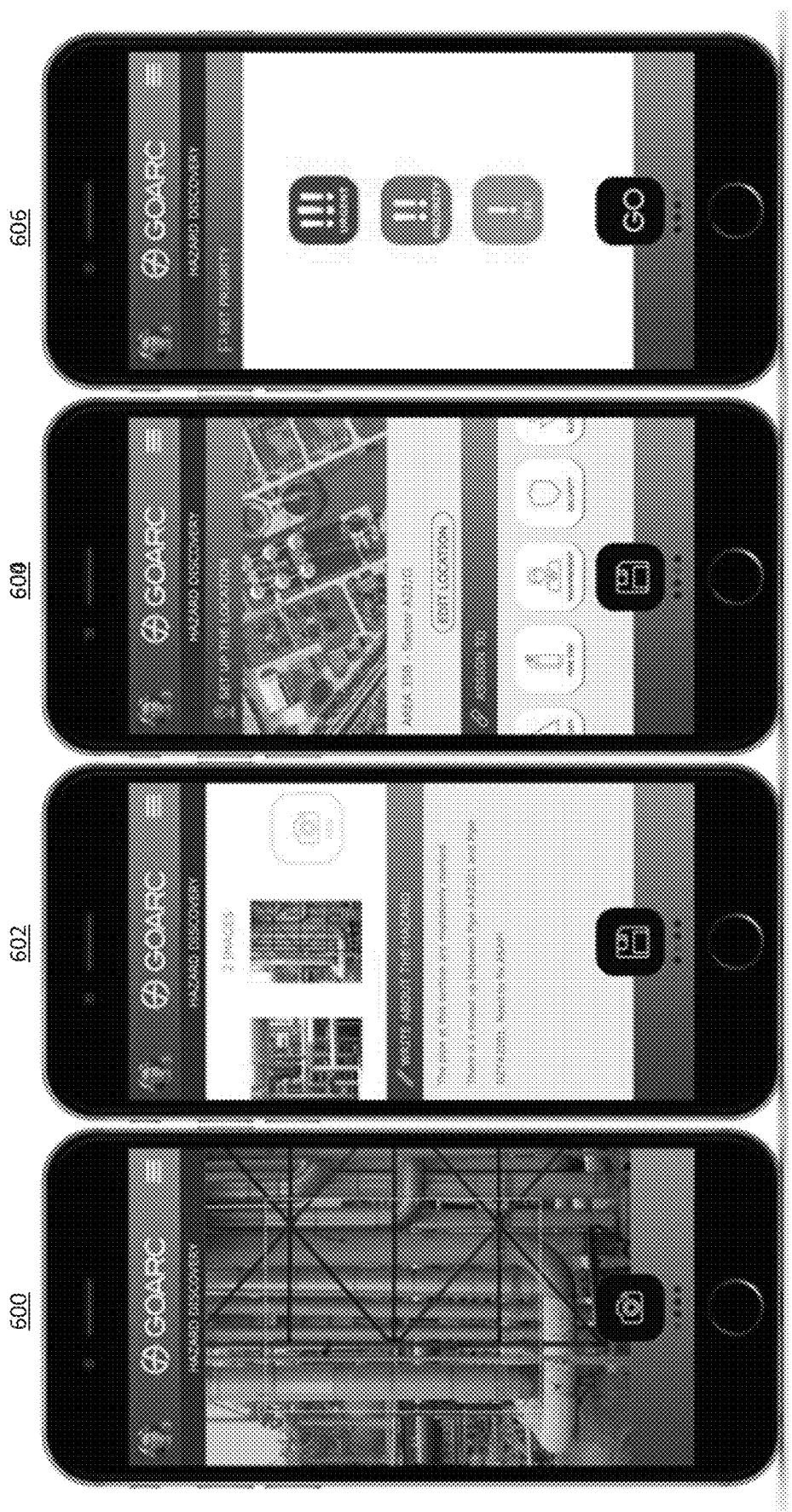
FIG. 6A-6C include screenshots illustrating different features of the exemplary system, consistent with the present disclosure.
Figure 6B:
Figure 6C:

FIGS. 6A-6C illustrate screenshots depicting different embodiments of the present disclosure. The screenshots may be displayed in different components of system 100 of FIG. 1, such as handheld communication device 105C and output unit 125. FIG. 6A depicts four screenshots that illustrate the process of reporting a hazard by an employee of the industrial environment. FIG. 6B depicts three screenshots that illustrate different types of notices that system 100 may provide to employees of the industrial environment. And FIG. 6C depicts a single screenshot illustrating how system 100 can assist in managing an on-going emergency event.

FIG. 6A depicts example screenshots 600, 602, 604, 606 that illustrate the process of reporting a hazard by an employee of the industrial environment. In one embodiment, each employee may be required to download a dedicated application associated with the industrial environment. The application may monitor the location of the employee while the employee is within an area associated with the industrial environment. In addition, the application may enable employees to report safety hazards they detect during their daily work. For example, the application may enable the employee to take one or more pictures of the hazard (e.g., screenshot 600), add written description of the hazard (e.g., screenshot 602), provide the location of the hazard (e.g., screenshot 604), and set the priority of the hazard (e.g., screenshot 606). In one embodiment, system 100 may determine the priority level associated with a reported event and use differently the information from the reports based on the priority level. For example, reports of events at a high priority level may be considered real-time information that may change the actual risk score of tasks currently being executed. In contrast, reports of events at a low priority level may be considered safety-related information that may change the predicted risk score of a task scheduled to take place.

FIG. 6B depicts examples of screenshots 610, 612, and 614 that illustrate different types of notices that system 100 may provide to workers of the industrial environment. Specifically, screenshot 610 illustrates a push notification that the employee may receive while his/her smartphone is locked. Typically, push notifications may be used only when an emergency situation occurs. Screenshot 612 illustrates location-based notices. The location-based notices (also referred to herewith as "location-based messages" or "location-based warnings") may be indicative of hazards located less than a predefined distance from the current location of the employee and may be specific to the employee role. For example, a maintenance personnel may receive a notice for fixing a light bulb less than 200 meters from his/her current location, and a cleaning personnel might receive a notice for fixing a wet floor less than 150 meters from their current location. Screenshot 612 illustrates a location-based personalized checklist. The personalized checklist informs the employee of actions needed to be executed in the employee's current location in order to comply with the task objective and/or work process procedures.

FIG. 6C depicts example screenshot 620 illustrating how system 100 can assist in managing an on-going emergency event. In response to a distress call from one of the employees, system 100 may cause a display of two screens for managing the emergency event. The left screen may show information on the employee and a real-time video feed of the on-going emergency event as it captured by the employee's smartphone. The right screen may show the employee's current location on a map, and additional information that may be relevant for managing the on-going emergency event. In the illustrated example of a fire that broke out in one of the storage facilities, the additional information may include the identity of the product stored in that facility, the wind direction, the location of closest fire extinguishing means, and more.

The foregoing description has been presented for purposes of illustration. It is not exhaustive and is not limited to the precise forms or embodiments disclosed. Modifications and adaptations will be apparent to those skilled in the art from consideration of the specification and practice of the disclosed embodiments. Additionally, although aspects of the disclosed embodiments are described as being stored in memory, one skilled in the art will appreciate that these aspects can also be stored on other types of computer readable media, such as secondary storage devices, for example, hard disks or CD ROM, or other forms of RAM or ROM, USB media, DVD, Blu-ray, or other optical drive media.

Computer programs based on the written description and disclosed methods are within the skill of an experienced developer. The various programs or program modules can be created using any of the techniques known to one skilled in the art or can be designed in connection with existing software. For example, program sections or program modules can be designed in or by means of .Net Framework, .Net Compact Framework (and related languages, such as Visual Basic, C, etc.), Java, C++, Objective-C, HTML, HTML/AJAX combinations, XML, or HTML with included Java applets.

Moreover, while illustrative embodiments have been described herein, the scope of any and all embodiments having equivalent elements, modifications, omissions, combinations (e.g., of aspects across various embodiments), adaptations and/or alterations as would be appreciated by those skilled in the art based on the present disclosure. The limitations in the claims are to be interpreted broadly based on the language employed in the claims and not limited to examples described in the present specification or during the prosecution of the application. The examples are to be construed as non-exclusive. Furthermore, the steps of the disclosed methods may be modified in any manner, including by reordering steps and/or inserting or deleting steps. It is intended, therefore, that the specification and examples be considered as illustrative only, with a true scope and spirit being indicated by the following claims and their full scope of equivalents.

What is claimed is:

1. A method for improving process safety in an industrial environment, the method comprising:
   receiving, by at least one processor, details of a task scheduled to take place in an industrial environment;
   retrieving, by the at least one processor, from a memory device data associated with the industrial environment, data that includes process safety data associated with a plurality of the industrial apparatuses;
   determining, by the at least one processor, at least one characteristic of the task based on the process safety data and the received details;

wherein, before the task takes place, the method includes:
obtaining, by the at least one processor, at least three types of safety-related information associated with the task scheduled to take place in the industrial environment;
determining, by the at least one processor, first synergy data from the at least three types of safety-related information and the at least one characteristic of the task;
determining, by the at least one processor, from the first synergy data, when a predicted risk score of the scheduled task is below a first threshold;
wherein, while the task is taking place, the method includes:
determining, by the at least one processor, based on data from a plurality of sensors located in the industrial environment, real-time information indicative of integrity of at least one of the plurality of the industrial apparatuses, at least some of the plurality of sensors including Global Positions Systems (GPS) receivers configured to provide geographic location data associated with a respective sensor;
determining, by the at least one processor, second synergy data from the at least three types of safety-related information and the real-time information including a geographic location of the at least one industrial apparatus, the second synergy data being indicative of a change in the integrity of the at least one industrial apparatus and including details on a situation in which the at least one industrial apparatus is used or maintained without complying with regulations;
determining, by the at least one processor, from the second synergy data that an actual risk score of the task has changed from the predicted risk score;
wherein, when the actual risk score of the task is above a second threshold, the method includes initiating, by the at least one processor, a remedial action in the geographic location of the at least one industrial apparatus to manage a hazard associated with the integrity of the at least one industrial apparatus.

2. The method of claim 1, wherein the at least one characteristic of the task includes at least one of: an estimated start time of the task, a type of industrial apparatus expected to be utilized in the task, an expected time duration of the task, potential accidents associated with the task, potential accidents associated with the type of industrial apparatus, types of materials expected to be used in the task, or types of tools expected to be used in the task.

3. The method of claim 1, wherein the at least three types safety-related information includes at least three of the following: work procedures associated with the task, information associated with a type of industrial apparatus expected to be utilized in the scheduled task, information associated with a location of the scheduled task, information associated with the scheduled task, information associated with tools expected to be used in the scheduled task, information associated with materials expected to be used in the scheduled task, information associated with a time of the scheduled task, information about calendar events, information associated with a weather expected to be during the scheduled task, information from periodic inspection tours, or information associated with the industrial environment.

4. The method of claim 1, wherein the process safety data includes at least two of: infrastructure blueprints, machinery inventory, and regulations about using and maintaining specific machines.

5. The method of claim 1, wherein, when the predicted risk score of the scheduled task is below the first threshold and above a third threshold, the method includes informing one or more individuals that a risky task is about to take place.

6. The method of claim 1, wherein, after determining that the predicted risk score of the scheduled task is below the first threshold, the method further includes providing to an employee associated with the task at least one of:
personalized training based on real safety incidents associated with a type of industrial apparatus expected to be utilized in the scheduled task;
recommendations on how to execute the task according to the work procedures;
information on existing hazards located in an area associated with the task; and
information on potential hazards located in an area associated with the task.

7. The method of claim 1, wherein the real-time information is obtained from at least one of: a plurality of cameras located in the industrial environment, one or more communication devices of employees in the industrial environment, wearable sensors of employees in the industrial environment, operational technology (OT) sensors associated with the plurality of the industrial apparatuses, environmental sensors, or sensors associated with working tools.

8. The method of claim 1, wherein the real-time information includes indications of employees actions that deviate from process safety procedures.

9. The method of claim 1, wherein, before initiating the remedial action, the method further includes determining a location of a real-time hazard that has a process safety source and a type of the real-time hazard.

10. The method of claim 9, wherein initiating the remedial action includes:
identifying an employee that responsible of handling the determined type of the real-time hazard; and
transmitting a message to the identifying employee, wherein the message includes the location of the real-time hazard.

11. The method of claim 9, wherein initiating the remedial action includes:
identifying an employee located within a distance of the real-time hazard, wherein the distance is determined based on type of the real-time hazard; and
transmitting a location-based warning to the identified employee.

12. The method of claim 9, wherein initiating the remedial action includes:
identifying an employee located within a distance of the real-time hazard, wherein the distance is determined based on type of the real-time hazard; and
transmitting a personalized location-based evacuation map to the identified employee.

13. The method of claim 9, wherein initiating the remedial action includes:
identifying an employee located within a distance of the real-time hazard, wherein the distance is determined based on type of the real-time hazard; and
transmitting instructions on how to fix or avoid the real-time hazard to the identified employee.

14. The method of claim 9, wherein initiating the remedial action includes displaying the real-time hazard on a personalized map together with a visual indicator of the real-time hazard's severity.

15. The method of claim 9, wherein initiating the remedial action includes performing an automatic shutdown of the at least one industrial apparatus to prevent predicted injuries or damages.

16. The method of claim 1, wherein, before initiating the remedial action, the method further includes predicting a location of a potential hazard and a type of the potential hazard; and initiating the remedial action includes at least one of:
- identifying an employee that responsible of handling the determined type of the potential hazard; and
- transmitting a message to the identifying employee, wherein the message includes the location of the potential hazard;
- identifying an employee located within a distance of the potential hazard, wherein the distance is determined based on type of the potential hazard; and
- transmitting a location-based warning to the identified employee;
- identifying an employee located within a distance of the potential hazard, wherein the distance is determined based on type of the potential hazard; and
- transmitting instructions on how to fix or avoid the potential hazard to the identified employee; and
- displaying the potential hazard on a personalized map together with a visual indicator of the potential hazard's severity.

17. The method of claim 1, wherein initiating the remedial action includes creating customized inspection tour based on detected locations of a plurality of potential hazards and real-time hazards.

18. A non-transitory computer-readable storage medium storing instructions that, when executed by at least one processor, causes the at least one processor to perform a method for improving process safety in an industrial environment, the method comprising:
- receiving, by the at least one processor, details of a task scheduled to take place in an industrial environment;
- retrieving, by the at least one processor, from a memory device data associated with the industrial environment, retrieved data that includes process safety data associated with a plurality of the industrial apparatuses;
- determining, by the at least one processor, at least one characteristic of the task based on the process safety data and the received details;
- wherein, before the task takes place, the method includes:
- obtaining, by the at least one processor, at least three types of safety-related information associated with the task scheduled to take place in the industrial environment;
- determining, by the at least one processor, first synergy data from the at least three types of safety-related information and the at least one characteristic of the task;
- determining, by the at least one processor, from the first synergy data, when a predicted risk score of the scheduled task is below a first threshold;
- wherein, while the task is taking place, the method includes:
- determining, by the at least one processor, based on data from a plurality of sensors located in the industrial environment, real-time information indicative of integrity of at least one of the plurality of the industrial apparatuses, at least some of the plurality of sensors including Global Positions Systems (GPS) receivers configured to provide geographic location data associated with a respective sensor;
- determining, by the at least one processor, second synergy data from the at least three types of safety-related information and the real-time information including a geographic location of the at least one industrial apparatus, the second synergy data being indicative of a change in the integrity of the at least one industrial apparatus and including details on a situation in which the at least one industrial apparatus is used or maintained without complying with regulations;
- determining, by the at least one processor, from the second synergy data, that an actual risk score of the task has changed from the predicted risk score;
- wherein, when the actual risk score of the task is above a second threshold, the method includes initiating, by the at least one processor, a remedial action in the geographic location of the at least one industrial apparatus to manage a hazard associated with the integrity of the at least one industrial apparatus.

19. A system for improving process safety in an industrial environment, the system comprising:
- a network interface configured to receive details of a task scheduled to take place in an industrial environment;
- a memory configured to store data associated with the industrial environment;
- at least one processor configured to:
  - retrieve from the memory data associated with the industrial environment, the retrieved data including process safety data associated with a plurality of the industrial apparatuses;
  - determine at least one characteristic of the task based on the process safety data and the received details;
- wherein, before the task takes place, the at least one processor is configured to:
- obtain at least three types of safety-related information associated with the task scheduled to take place in the industrial environment;
- determine first synergy data from the at least three types of safety-related information;
- determine from the at least one characteristic and the first synergy data when a predicted risk score of the scheduled task is below a first threshold;
- wherein, while the task is taking place, the at least one processor is configured to:
- determine, based on data from a plurality of sensors located in the industrial environment, real-time information indicative of integrity of at least one of the plurality of the industrial apparatuses, at least some of the plurality of sensors including Global Positions Systems (GPS) receivers configured to provide geographic location data associated with a respective sensor;
- determine second synergy data from the at least three types of safety-related information and the real-time information including a geographic location of the at least one industrial apparatus, the second synergy data being indicative of a change in the integrity of the at least one industrial apparatus and including details on a situation in which the at least one industrial apparatus is used or maintained without complying with regulations;
- determine from the second synergy data that an actual risk score of the task has changed from the predicted risk;
- wherein, when an actual risk score of the task is above a second predetermined threshold, the at least one processor is configured to initiate a remedial action in the geographic location of the at least one industrial apparatus to manage a hazard associated with the integrity of the at least one industrial apparatus.

* * * * *